United States Patent [19]
Rak

[11] 4,143,010
[45] Mar. 6, 1979

[54] HIGH RETENTION WOOD PRESERVATIVE COMPOSITION

[75] Inventor: Jaromir R. Rak, Ottawa, Canada

[73] Assignee: Canadian Patents and Development Limited, Ottawa, Canada

[21] Appl. No.: 890,518

[22] Filed: Mar. 27, 1978

Related U.S. Application Data

[63] Continuation-in-part of Ser. No. 657,398, Feb. 12, 1976, Pat. No. 4,085,251, which is a continuation-in-part of Ser. No. 417,404, Nov. 19, 1973, abandoned.

[51] Int. Cl.$^2$ .............. C08L 23/12; C08L 25/06; C09D 3/80; C09D 5/14
[52] U.S. Cl. ............... 260/23 S; 106/2; 106/18; 106/15.05; 260/23 AR; 260/23 H; 260/28.5 R; 260/28.5 A; 422/40 P
[58] Field of Search ............ 106/2, 18, 15 R; 260/23 AR, 23 S, 23 H, 28.5 A, 28.5 R

[56] References Cited

U.S. PATENT DOCUMENTS

| | | | |
|---|---|---|---|
| 3,200,003 | 8/1965 | Bescher | 427/440 |
| 3,249,499 | 5/1966 | von Schmeling et al. | 424/276 |
| 3,600,408 | 8/1971 | Bursack et al. | 424/347 |
| 3,967,011 | 6/1976 | Dunn et al. | 427/440 |

FOREIGN PATENT DOCUMENTS

1281911   7/1972   United Kingdom ............ 427/393

OTHER PUBLICATIONS

American Wood-Preservers' Association Proceedings (1963), pp. 68–76.
American Wood-Preservers' Association Proceedings (1971), pp. 37–46.

*Primary Examiner*—Ronald W. Griffin
*Attorney, Agent, or Firm*—Alan A. Thomson

[57] ABSTRACT

A wood preservative composition having deep penetration capability, leaving a clean surface and imparting high retention of active preservative within the wood, which consists primarily of (a) an organic wood preservative agent, (b) a hydrophobic agent, and (c) small amounts of an amorphous vinylic-type polymer, in a penetrating organic solvent. The preservative may be pentachlorophenol, an oxathiin compound or other preservative preferably of low mammalian toxicity. The hydrophobic agent may be fatty acids and their esters, fatty alcohols and paraffin waxes. The amorphous polymer may be a polystyrene, a polymethylmethacrylate, a polyvinylformal, an atactic polypropylene or other such amorphous polymer. The penetrating solvent may be most suitably chloroform, methylene chloride, trichloroethylene or liquefied petroleum gas, although others may be used. Solutions suitable for deep penetration pressure treatment are preferred. The active preservative penetrates and becomes immobilized within the penetrated wood microstructure.

11 Claims, 8 Drawing Figures

FIG. 1a
PCP

FIG. 1b
PCP + VACUUM

FIG. 2a
PCP + ADDITIVES

FIG. 2b
PCP + ADD. + VACUUM

HIGH RETENTION WOOD PRESERVATIVE COMPOSITION

CROSS-REFERENCE TO RELATED APPLICATIONS

This application is a continuation-in-part of application 657,398 filed Feb. 12, 1976, now United States Pat. No. 4,085,251 (which was a continuation-in-part of application 417,404 filed Nov. 19, 1973, now abandoned).

FIELD OF THE INVENTION

This invention is directed to wood preservation primarily from biological attack using compositions causing the immobilization of active ingredient within the wood microstructure.

DESCRIPTION OF THE PRIOR ART

Contemporary systems for heavy duty preservation of timber (such as utility poles, piles, posts, bridge beams, glulams, lumber, etc.) frequently employ pentachlorophenol (PCP) as a reliable heavy duty preservative. Application to leave a clean surface involves processes like "Cellon" (trademark) LPG impregnation or the methylene chloride solvent treatment to drive the PCP into the wood providing a reasonably clean surface requiring no seasoning. However material treated with PCP by these processes, suffers from disadvantages such as loss of PCP from the wood (sublimation) and low water repellency and weather resistance. Both disadvantages result in lowering of service life when compared with wood treated by the older conventional PCP-oil-borne systems, and also in limitations to use of the treated wood in closed poorly ventilated areas, e.g. basements. (The PCP-oil-borne systems have the major disadvantages of wood discolouration, oily unpaintable surfaces, stickiness and dirt retention.)

These disadvantages (using the so-called clean processes) can be partially solved by raising the amount of preservative incorporated into the wood thus retaining the concentration level above or close to the effective threshold value even after loss of some preservative resulting in an acceptable service life. Adequate water-repellancy and PCP retention, and elimination of the health hazard due to vapours of PCP, can be realized by additional painting or top-coating of the wood surface. Such additional treatments (use of excess PCP and/or top-coating) considerably increase the cost of treated wood and in many cases are not economical. Heavy loadings of polymers and/or resins have been incorporated in PCP preservative compositions to completely seal the wood surface as in British Pat. No. 1,281,911 Blunt et al. However, loss of penetrability and cost render this unacceptable in many applications. See Example 6 below.

It would be desirable to have a clean heavy duty wood preservative system having penetration of preservative equivalent to the methylene chloride-PCP system, and water-repellency and service life at least as good or better than the PCP-oil-borne systems.

SUMMARY OF THE INVENTION

According to the invention, a wood preservative composition is provided having deep penetration capability, imparting a clean surface and good service life to the wood substrate. The composition comprises:

(a) an organic wood preservative agent;

(b) a hydrophobic agent selected from fatty acids and their esters, fatty alcohols and various waxes, suitably having at least ten carbon atoms in the longest chain in the molecule;

(c) an amorphous vinylic-type polymer in amounts of up to about 30% by weight based on total solids; and (d) a penetrating organic solvent for (a), (b) and (c).

The preservative should be highly toxic to microorganisms which attack wood, and is suitably pentachlorophenol, an oxathiin antimicrobial, tributyl tin oxide or other organic biocide. The composition will preferably include from about 1 to about 6% w/v of preservative, although slightly more than this could be operative (up to about 10% or the limit of solubility).

The hydrophobic agent is a water-insoluble solid or semisolid from fatty acids, fatty acid esters, fatty alcohols and various waxes. These acids, esters, fatty alcohols, waxes and mixture thereof should be soluble in the solvent to at least about 0.5% w/v, preferably about 2–4%. There is usually no advantage in including more than about 5% although up to the limit of solubility would be operative. Examples include decanoic acid, lauric acid, palmitic acid, stearic and oleic acids, octadecanol, ethyl laurate, methyl stearate, propyl stearate, benzyl laurate, phenyl laurate, and paraffinic waxes. Those hydrophobic agents having higher melting points, such as lauric acid (44° C.), palmitic acid (63° C.), stearic acid (70.1° C.), paraffin waxes etc., are preferred to those with lower melting points such as nonanoic acid (15° C.), decanoic acid (31.5° C.) or oleic acid (16.3° C.). Paraffin waxes have been tested and provided the same degree of water repellency as the fatty acids with higher melting points (>44° C.). Waxes are usually the cheapest, although crude mixtures of acids or esters would also be low-cost agents.

The vinylic-type polymer must be amorphous and soluble in the same solvent as the other components to at least about 0.2% w/v, preferably about 0.3 to 1%. The amount of polymer will normally not exceed about 30% by weight of total solids in the composition. As low as about 3% of the solids would be operative. A preferred range is about 5 to 20% of the solids. The main function of the polymer is to immobilize or reduce loss of preservative while at the same time increasing water repellency. Thus the vinylic polymer will be highly compatible with the preservative. The degree of polymerization of the polymer is selected so that the polymer has sufficient solubility in the organic solvent. The amorphous nature of the polymer is of primary importance in defining the suitability of this component. The amorphous condition enables effective and uniform enmeshing of the preservative and the hydrophobic agent (usually both crystalline) among the polymer chains when deposited in the wood. A crystalline polymer, after solvent removal, would form areas of polymer separate from the other components, and would not have the required protective function. Examples can be selected from the group including polystyrenes, polymethacrylates (e.g. methylmethacrylates or butylmethacrylates), atactic polypropylenes, polyvinylformals, and other amorphous vinylic-type polymers.

The common solvent for dissolving all three main components into one solution, is an organic solvent of lipophilic nature i.e. a fat solvent. Preferred are the highly halogenated lower aliphatic hydrocarbons with low boiling point (less that 100° C.) and preferably which are nonflammable, such as tetrachloromethane (carbon tetrachloride), trichloromethane (chloroform), bromochloromethane, 1,1,1-trichloroethane, bromodichloromethane, trichloroethene, 1,2-dichloromethane (methylene chloride) and mixtures thereof. Those solvents with higher boiling point (more than 100° C.) and preferably non-flammable (e.g. trichlorethylene, tetrachloroethylene) can be used with advantage in applications like spray, brush or dip treatments. Also a highly volatile liquefied petroleum gas (LPG), usually with cosolvent, can be used as in the "Cellon" (trademark) process.

The solvent's ability to dissolve all three components into one solution is the main criterion for its selection. Non-flammability, though preferred, is not an essential feature of the solvent. Where deep pressure treatment of large forest products (such as poles or square timber) is required, the solvents should have low polarity or be nonpolar (with dielectric constant < 15.0) in order to penetrate fast and deep into wood while carrying all of the additives and they should have a low boiling point (< 100° C.) because almost full recovery of solvent is necessary. In non-pressure treatments like dip, brush or spray treatments or treatments of smaller forest products, the requirements for polarity and boiling point of solvent are less strict (solvents with higher polarity and higher boiling point can be used in this case). Boiling point and polarity are not necessary criteria for solvent definition. Such other solvents can be aromatic, for example, benzene, toluene, or xylene. These aromatic solvents dissolve PCP, fatty acids, paraffin waxes and polystyrene as well. But they could not be used with e.g. polyvinylformal as this polymer is not solubilized by them. However polyvinylformal could be used in chloroform solution. On the other hand, aliphatic hydrocarbons e.g. Varsol (trademark) while solvents for PCP, fatty acids and paraffin waxes, do not dissolve the polymers.

The preservative composition can be applied by various methods used in the industry; for example by impregnation of square or round timbers (under pressure) or by dip, spray or brush treatment of lumber or fabricated structures. Any impregnation method employed for an oil-free system can be used; thus in addition to LPG-cosolvent systems, the methylene chloride treatment (MCHP) is also operative.

All three components in the preservative solution penetrate into the wood during application, and after the evaporation of solvent the composition changes into a homogeneous mixture of preservative and hydrophobic agent, both immobilized or retained in a web, film or matrix structure of polymer. The penetrated wood is left with a clean surface. Thus there is formed in the wood a "complex network of closed microsegments" in which all penetrated cells in the wood are sealed by a continuous system of barriers. Each barrier is protecting each closed microsegment of the wood in 3 ways i.e. against (1) blooming or sublimation loss of preservative, (2) wetting and leaching of the preservative, and (3) biological attack and degradation. The hydrophobic agent reliably increases the water-repellency but it cannot adequately immobilize the preservative in the wood microstructure. The polymer on the other hand forms impermeable barriers (even when in low concentration) effectively limiting sublimation loss and confining the preservative within the cell or closed microsegment - but in the small concentration used is unable to bestow adequate water-repellency on its own.

If the hydrophobic agent was omitted, an increase of polymer component would be required. However, because the polymer has a high molecular weight compared to the hydrophobic agent, a treating solution containing larger amounts of polymer would penetrate less rapidly into wood. It should be emphasized that the excellent penetrability of the oil-free systems (either MCHP system or Cellon System or others as in the present invention) to carry PCP deeply into wood is one of the major advantages of these systems. Reduction of penetrability due to polymeric ingredients in significant concentrations would make the preservative system less effecient. Hydrophobic agents according to this invention are low molecular compounds which do not reduce the penetrability of the solutions significantly (neither do the low concentrations (up to about 1% w/v) of amorphous polymer).

A suitable amount of preservative deposited in the wood would range from about 0.05 to about 2.5 lbs. (total solids) /cu. ft. for effective preservation. Somewhat more or less than this may be useful in certain cases.

The invention is illustrated by the following Examples.

EXAMPLE 1

The Accelerated Sublimation Test

In order to determine the influence of chemical components in the preservative composition on loss of preservative (PCP) under accelerated sublimation conditions, three solutions have been prepared, separately, in carbon tetrachloride as a solvent (in percent w/v).

I. Solution: PCP (3.5%) as a preservative.
II. Solution; PCP (3.5%) and stearic acid (3.5%) as the hydrophobic agent.
III. Solution: PCP (3.5%) stearic acid (3.5%) and polystyrene (0.7%) as the organic polymer.

The same volume of each solution (0.07 ccm/sq.in.) has been poured on the surface of glass template and the solent evaporated at room temperature leaving solid deposits of each sample. Then these deposits of the 3 different preservative compositions (I—II—III), in which the amount of preservative (PCP) was the same, were exposed to vacuum at room temperature in order to accelerate the loss of components. The loss of weight of each single deposit was checked periodically and is expressed in FIG. 1 in percent of original weight of preservative (PCP).

This experiment clearly shows that the admixture of organic polymer along with the hydrophobic agent allows a loss of PCP of only about 36%, which is a 63% reduction of PCP sublimation compared to the control sample. When PCP is protected by no additive it has evaporated under same conditions to the extent of 99%.

Figure 1:
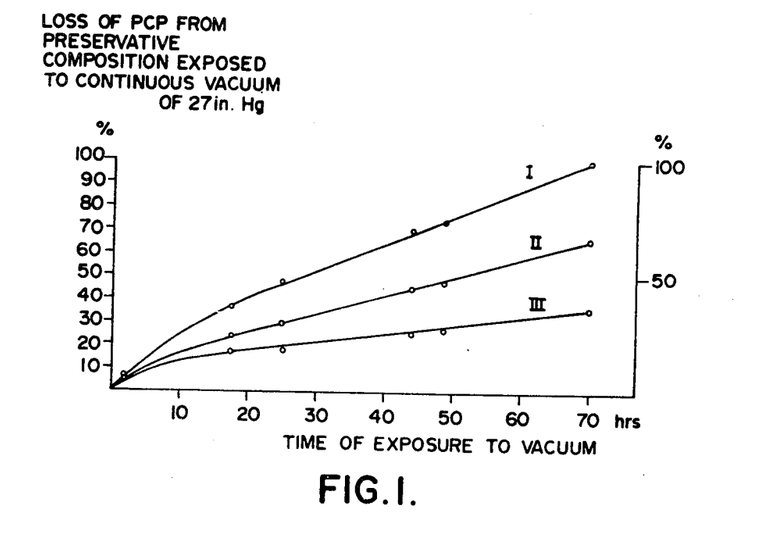
FIG. 1 is a graph showing results of accelerated sublimation tests.

The reduction of PCP sublimation on account of the presence of 0.7% of polymer (polystyrene) amounts to 30%, while the hydrophobic agent (stearic acid) in a much higher concentration (3.5%) than the organic polymer shows a reduction of PCP sublimation of only 34% from the control (all percentages are as shown in FIG. 1). The experimental evidence proves the high efficiency of the organic polymer component in very low concentrations in reducing the preservative (PCP) loss due to evaporation.

EXAMPLE 2

The Hydrophobicity of Wood Treated by Preservatives

Figure 2:
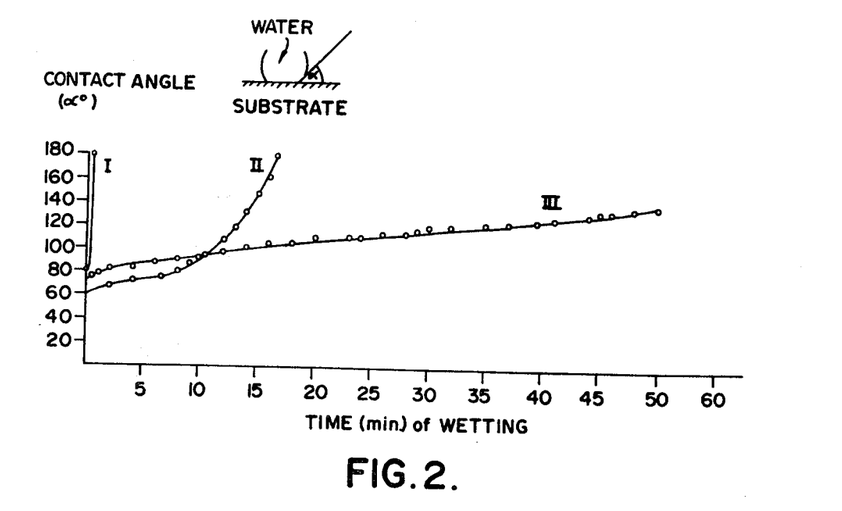
FIG. 2 is a graph showing the hydrophobicity (contact angle) on treated surfaces.

The same solutions of preservative compositions (I—II—III), as in Example I have been used for impregnation of red pine wood samples in order to determine the effect on hydrophobicity of wood. After the samples of wood have been fully saturated by solutions I—II—III, the solvent was then evaporated at room temperature during the next 24hours, leaving solid deposits of the components in the wood. Measurements of contact angles of the surface of water drops on pertinent wood samples were made to show the relative hydrophobicity. The sooner the water soaks in the surface of wood (contact angle 180°) the lower the hydrophobicity of wood and vice versa. FIG. 2 shows clearly that wood treated by PCP alone, soaked water readily (within 40 seconds), while the wood treated by the preservative composition comprising hydrophobic agent and amorphous organic polymer (sample III) did not allow water to soak into the surface completely even after 50 min. The hydrophobic agent (stearic acid in sample II) itself improved significantly the hydrophobicity but the water soaked into the wood after more than 16 min.

EXAMPLE 3

Microscopic Tests of Preservative Composition

In order to illustrate further the protective function of the polymer in the mixture of preservative with hydrophobic agent, photomicrographs have been taken of preservative compositions deposited in thin layers (from solution I-II-III, as in Example 1). In the solid deposit of preservative from solution I (PCP only) and from solution II (PCP and stearic acid $^{one}$/one respectively), the hydrophobic agent (stearic acid) is seen to partially cover the crystals of preservative (PCP). The same picture can be seen when the organic polymer is added to solution II in order to make solution III and dried at the beginning of an evaporation test. But the major effect or protective function of the polymer (polystyrene) present in solution III is to reduce the loss of preservative, and this is seen after the accelerated evaporation test as in Example 1 has been completed. At this point (after 70 hours under vacuum) when the control sample from solution I (PCP only) protected by no additive has 99% disappeared, the sample from solution II (PCP and stearic acid) shows that PCP crystals have also disappeared from major part of sample.

However, the sample in which PCP with stearic acid has been protected against evaporation by further admixture of 0.7% (w/v) of amorphous polymer (polystyrene), demonstrated clearly the protection of PCP crystals which were partially embedded in a transparent layer of polystyrene (along with particles of stearic acid).

Comparison of the photomicrographs showed the important function of the polymer as a necessary component in the preservative composition to protect the preservative (PCP) against loss due to sublimation.

EXAMPLE 4

Soil Block Tests

Tests were carried out to demonstrate the toxicity of treated wood samples to wood-destroying fungi, i.e. to show that the PCP is not rendered ineffective. The composition of the present invention was compared with PCP itself in a standard test (AWPA-M10) against two wood-destroying fugi *Poria vaporaria* and *Coniophora cerebella* using white pine.

There was little difference in toxicity between PCP and the composition of the present invention (e.g. 3.5% PCP, 1% stearic acid and 0.7% polystyrene) although a slight benefit for the latter appeared at low retention levels. Statistical analysis showed no significant difference between PCP itself and this particular formulation at the tested retention levels of 0.05, 0.10, 0.25, 0.75 and 1.75 lbs. PCP/cu. ft. However, the present invention would bestow much prolonged effectiveness over PCP alone.

EXAMPLE 5

The following formulation was prepared:
3.5% w/v PCP,
0.8% paraffin wax, M. P. 51.5° C. and
0.6% polystyrene,
in carbon tetrachloride as solvent. Samples of Western Red Cedar, 1 inch by ¾ inch by ½ inch, were impregnated with this preservative for 1 hour under a vacuum of 25 inches of mercury, and subsequently air-dried.

In the water-repellency test, the contact angle on the treated sample was initially similar to line III in FIG. 2. After 37 min. the contact angle had reached 180°. Considering the lower percentage of hydrophobic agent used, this is a very acceptable water-repellency.

The formulation of the present invention has been tested on various wood species and it has been shown that the wood remains undiscoloured having a natural appearance, that the surface has good water repellency, and that toxicity and PCP retention remain high for prolonged service life.

EXAMPLE 6

For comparison with the Blunt et al British Pat. No. 1,281,911, two formulations were made up as follows to a constant PCP level. (Percents are on a weight/volume basis). It was necessary to heat the Blunt et al formulation to 55° C. on a water bath to obtain dissolution.

| Component | Present | Blunt et al |
|---|---|---|
| PCP % | 4.5 | 4.5 |
| Polystyrene % | 1 | 4.5 (100% of PCP) |
| Paraffin wax % | 4.5 | — |
| Escorez resin % (Esso) | — | 9% (200% of PCP) |
| Solvent | Chloroform | Solvent Naphtha |

The main difference between these two types of formulations is the ability to penetrate wood (the present one is designed for deep penetration for heavy duty, while Blunt et al's is designed for surface blocking treatment). To accentuate penetration, both formulations were tested in pressure treatments carried out simultaneously on spruce wood samples (five samples for each formulation). The samples 1 × 1 × 12 inches were treated at 20 psi pressure for two hours while immersed in the preservative liquids. After the treatment, the samples were cross cut in the center and the preservative liquid penetration marked and measured in the transverse direction. A second series of pressure treatments was carried out as before but for four hours, and the penetration again marked and measured at the centers (where not affected by end penetration). The results were as follows.

| Average Penetration Depth (Inch) in Spruce | | | |
|---|---|---|---|
| Present | | Blunt et al | |
| Two hours | Four hours | Two hours | Four hours |
| 0.2 | 0.3 | 0.07 | 0.1 |

The penetration of the Blunt et al formulation was only about one third that of the present formulation. The sample cross sections were carefully examined after the solvent dried off and the PCP penetration was observed to be the same as the solvent for the Rak formulation, but PCP was left behind the solvent penetration for the Blunt samples. This degree of penetration for the Blunt et al formulation would render it unacceptable for commercial pressure treatment use for which the present formulation is primarily designed. It is clear that the Blunt et al formulation was designed only for surface pore blocking and improved paint adhesion, not for deep penetration of the wood.

In order to meet American Wood Preserver's Association and Canadian Standards Association 080 specifications for pressure treatment penetration of preservative, the penetration must be substantially equivalent to that of the "Dow Process" PCP-in-methylene chloride system (see AWPA Proceedings, Vol. 68, 1972, page 148 etc.) A preservative uptake experiment was carried out by immersing sample of white spruce in the preservative solutions at atmospheric pressure, the preservative solutions being (a) PCP in methylene chloride (5%), "Dow Process" preservative, (b) PCP (5%) + paraffin wax (3.5%) + polystyrene (1%) in methylene chloride, i.e. present preservative. The uptake of preservative solution (volume) was measured and plotted against time of immersion for (a) and (b) solutions and the curves were seen to be substantially identical. Thus the present formulation (b) will meet the penetrability standards (but the Blunt et al formulation would not).

EXAMPLE 7

Comparative Penetration Test by Solution Uptake

Sorption and diffusion of solutions in wood without pressure conditions helps to carry the solutions further into wood (even after a main preservative treatment by a high pressure process). Faster uptake of preservative solution indicates better penetrability of the solution and results in deep preservative penetration in wood.

Tests were carried out under non-pressure conditions, on spruce blocks of size 1.05 × 1.05 × 1.05 inch, with 10 replicas for each tested solution. Since the specific gravity of the test solutions varied, solution uptake was measured as volume (not weight) of the solution taken up by the blocks. Average values of solution uptake were determined.

The following compositions were tested: (solutions with % on weight/volume basis)
1. 4.5% pcp in chloroform
2. 4.5% pcp in methylene chloride
3. 4.5% pcp
   3.5% stearic acid
   1.0% polystyrene in methylene chloride
4. 4.5% pcp
   3.5% stearic acid
   1.0% polymethylmethacrylate in chloroform
5. 4.5% pcp
   3.5% stearic acid
   1.0% polyvinylformal in chloroform
6. 4.5% pcp in pole oil Results of solution uptake by volume of air dried spruce samples are shown in Table 1. a. The non-pressure solution uptake during 24 hour period clearly indicated the variation between fast and slow penetration of the preservative compositions. b. Preservative compositions Nos. 1, 2 and 3 have almost identical rates of solution uptake and showed the greatest penetration. c. Preservative compositions No. 4 and 5 have a slightly slower rate of solution uptake, but they belong, according to the trend of solution uptake between 5 and 24 hours exposure, to the same group of deeply penetrating preservative solutions as 1, 2 and 3 with relatively high rates of penetration. d. The typical oil solution of pcp #6 penetrated into wood at a significantly slower rate than the #1-#5 preservative compositions. These #1-#5 compositions showed, after 24 hour exposure, 27 to 46% higher solution uptake by volume than the oil solution. e. Staining of penetrated sections revealed the pcp had fully penetrated with the solvent for #1-#5, while for #6, pcp penetration was relatively superficial.

TABLE 1

| Average Volumes of Preservative Solution Taken up by One inch Cube Spruce Samples | | | | | | | |
|---|---|---|---|---|---|---|---|
| Time of Exposure | | Preservative Solution Number | | | | | |
| hours | mins. | 1 (ml) | 2 (ml) | 3 (ml) | 4 (ml) | 5 (ml) | 6 (ml) |
| 1 | 25 | 1.00 | 1.03 | 1.01 | 1.15 | 1.15 | — |
| 2 | 25 | 1.25 | 1.24 | 1.26 | 1.33 | 1.22 | 1.30 |
| 5 | 30 | 1.62 | 1.62 | 1.61 | 1.62 | 1.48 | 1.50 |
| 8 | 30 | 1.93 | 1.94 | 1.93 | 1.86 | 1.72 | 1.65 |
| 24 | 30 | 3.00 | 2.98 | 3.01 | 2.70 | 2.60 | 2.05 |

EXAMPLE 8

Immobilization of Preservative in the Wood Structure

This Example illustrates the difference between immobility and high retention of preservative deposited in wood by the composition of this invention, and preservative deposited without any additives from the standard solution in methylene chloride (Dow Process).

Two homogeneous samples of spruce wood, 2 × 2 × 18 inch each, containing sapwood, were treated with two different solutions:
Sample A: treated with 4.5% w/v of PCP in methylene chloride, corresponding to commercial "Dow Process".
Sample B: treated with 4.5% w/v of PCP
   4.5% w/v stearic acid
   1.0% w/v polystyrene in methylene chloride solution. After pressure treatment (at 120 psi for 7 hours, at room temperature) the samples were taken out of the retort, cross-cut and penetration of PCP was detected by application of stain (in the form of a spray) specific for PCP detection, known as "Penta-Check" (trademark) according to AWPA Standard A3- 68. The depth of penetration on cros-sectioning in both samples A and B was approximately 0.4 inch. Similarly to Example 7, the penetrations for solutions A and B under pressure were equivalent i.e., the additives of the invention did not significantly retard penetration in either solution uptake or pressure treatment.

After the PCP penetration was detected in the sapwood area in both samples to approximately in the same depth, the stained surface of the cross-section was removed from both samples by additional cutting away of a slice of the cross-section to provide unstained surfaces of the treated wood.

From both samples, microsections were cut from the wood tissues, approximately 0.35 –0.37 inch from the surface in the radial direction, i.e. within the area, where the PCP was positively detected by previous staining. Numerous microscopic sections (transverse) were made from both samples (A and B) separately. From each of both groups of microsections, typical sections were again microscopically stained with a Silver-Copper complex (which is the basis of the "Penta-Check") to detect again PCP in the microsections. Other typical unstained microsections were mounted into microscopic slides and without any staining examined microscopically. On the viewed microsections of treated wood typical spots were selected where the cell obviously contained significant deposits of PCP, and photographed, at the same magnification. Photographed microsections from sample A and B were then carefully removed from the slides, gently dried off by a touch of absorbent paper at the corner of the microsections, and transferred into a vacuum desiccator by a micromanipulator. The desiccator was then closed and very slowly evacuated. When the vacuum reached 29.5 inch Hg, the desiccator was sealed and the microsections left for 7 days (exactly 164 hours). Then the desiccator, still at 27 inch vacuum, was slowly filled with air, opened and the microsections transferred onto glass slides and mounted for microscopic examination. This exposure under the same vacuum conditions (29.5 –27 inch Hg) for 7 days gave accelerated sublimation of PCP. The accelerated vacuum test is considered as an accurate simulation of the effect of ordinary atmosphere for an extended time. The microscopic slides were carefully examined, the same spot of each microsection was found (as photographed before vacuum exposure) and rephotographed (at the same magnification) for comparison.

Two pairs of photomicrographs are shown as FIGS. 1 (a) and 1 (b), and as FIGS. 2 (a) and 2 (b), being typical of observations of as many as 50 microsections. The first pair, FIGS. 1 (a) and 1 (b), depict the same microstructure, at a magnification of 455 times, impregnated with PCP before 1 (a) and after 1 (b) the vacuum exposure. The second pair of photomicrographs 2 (a) and 2 (b), also at 455x, are for PCP + additive formulation of the present invention and depict the same cells of the spruce micro-structure before 2 (a) and after 2 (b) the 164 hour vacuum exposure.

The identical cells shown on microsections a and b of FIGS. 1a, 1b and 2a, 2b, are numbered and marked by letters for comparison. During handling of microsections between the first photographing and the second, the microsections were accidentally turned upside down so they formed mirror images. However, the same cells and lumina are shown.

OBSERVATIONS (EXAMPLE 8)

The microsections of spruce treated under the same treating conditions with 2 different preservative solutions showed the same penetration depth.

Figure 1A:
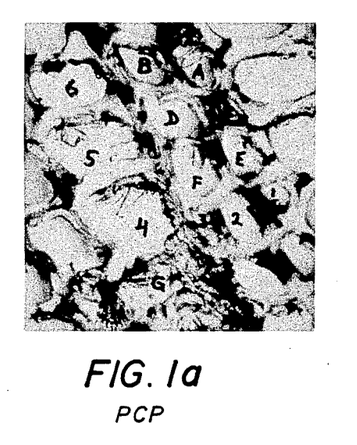
FIGS. 1a and 1b are photomicrographs at 455x of a wood microstructure penetrated with PCP alone, before and after vacuum exposure.
Figure 1B:
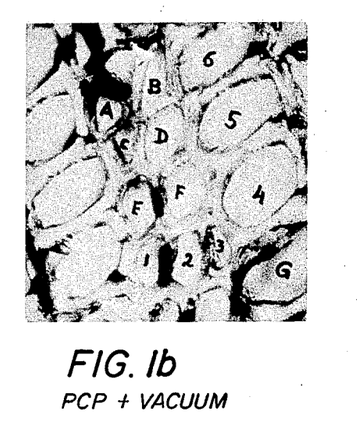

In FIG. 1 (a) cells designated 1, 3, 4, 5, A, F and G have crystals, whiskers or deposits of PCP associated therewith. In FIG. 1 (b), the same cells are devoid of PCP due to the vacuum exposure.

Figure 2A:
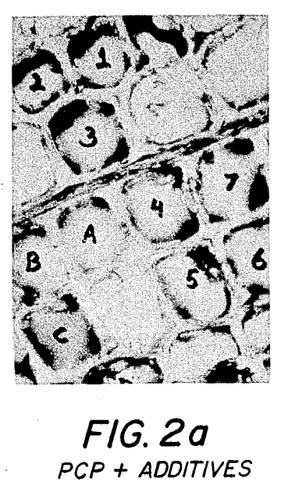
FIGS. 2a and 2b are photo-micrographs at 455x of a different wood microstructure penetrated with the formulation of this invention before and after vacuum exposure.
Figure 2B:
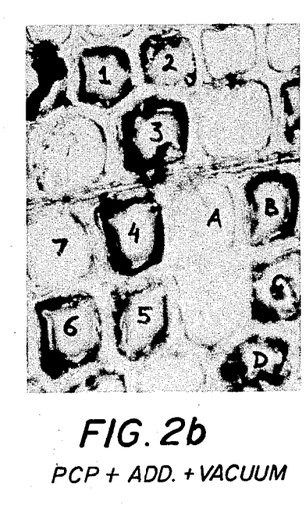

In FIG. 2 (a), cells 1, 2, 3, 4, 5, 6, 7, A, B, C and D have deposits which include PCP associated therewith. In FIG. 2 (b), cells 1, 2, 3, 4, 5, 6, B, C and D still have substantial deposits including PCP after the vacuum treatment. Only two cells, 7 and A, have lost visible deposits. The PCP-containing deposits are visible between the cells or as a layer around the cell lumen.

Thus PCP alone had disappeared after vacuum exposure FIG. 1 (b), while PCP plus the polymer and water-repellent additives substantially withstood the same vacuum exposure. The new formulation caused immobilization and high retention of the active preservative.

Another important feature of the new formulation is the regular distribution of PCP enmeshed with additives around the cell lumina. Microscopic staining showed that PCP was evenly distributed around the cell lumina in the preservative deposits in the cells. PCP does not separate or migrate from the additives in the microstructure of the wood. On the other hand, PCP without these additives, was deposited on the cell walls in individual spots (in form of crystals, see FIG. 1a) rather than being deposited on the cell lumen in a continuous layer (as shown in FIGS. 2a and 2b).

The microscopic sections treated with PCP + additives also showed considerable water repellency (as proven earlier by tests of water-repellency rating). As seen in FIGS. 2a and 2b, those cells containing deposits of preservative around the lumina are also darker. It is evident the preservative prevented the water (used for mounting of the microsection) from entering into the lumen so that an air bubble was trapped in the lumen and visible darkening of the lumen resulted. When no preservative (PCP + additive) was present (such as in FIG. 2b, in cell 7 and A) water entered the lumen and visibly clear lumen resulted. It is evident that the microsections with PCP only (such as in FIG. 1a) contained preservative in form of crystals which were separate from each other on the cell wall in the lumina of cells, and because these crystals are not highly water repellent, water entered into all lumina (and a clearer picture resulted).

Recently more interest is being shown in biocides (fungicides, bactericides) of low mammalian toxicity. Oxathiin derivatives have been developed as systemic plant fungicides (see inter alia United States Pat. No. 3,249,499). Various oxathiins and other carboxanilides having fungicidal properties are described by R. J. W. Cremlyn in International Pest Control 15(2) 1973 pages 8 – 11. The structure is common to these fungicides. The double bond is part of an appropriate ring structure, usually a heterocyclic ring. Several of these carboxanilides are on the market as seed dressings or systemic fungicides against rusts, smuts and bunts of cereals and some ornamentals. These fungicides generally have low mammalian toxicity.

Preliminary tests indicated that oxathiin derivatives (deposited from methanol solutions) would have a preservative effect in wood subject to decay by fungi (see R. S. Smith in Environment Canada — Bimonthly Research Notes 26(3) 1970 page 24).

The following examples illustrate the use of these derivatives in the wood preservative system of the present invention. The following two compounds were used in the tests:

D-18 or carboxin = 2,3-dihydro-5-carboxanilido-6-methyl-1,4-oxathiin

D-20 or oxycarboxin = 4,4-dioxide analog of D-18

EXAMPLE 9

Leaching Resistance Test

Comparable samples of spruce sapwood were saturated with four different preservative solutions as follows:

Solution I 5% w/v D-18 in chloroform
Solution II 5% w/v D-20 in chloroform
Solution III 5% w/v D-18
    1.4% w/v paraffin wax
    1.0% w/v polystyrene in chloroform
Solution IV same as III but with 5% w/v D-20.

Uptake of preservative was calculated from the weight increase. Chloroform solvent was removed from the samples by air drying followed by drying in the oven at 105° C. for 4 hours. Each sample was leached with a standard volume of distilled water at room temperature. Every two hours the water surrounding each sample was removed for spectrophotometric measurement and was replaced by another standard volume of fresh distilled water. Total leaching time was 140 hours. The concentration of D18 and D20 in the leach water was determined by comparing specific absorbance in UV light with the absorbance of known concentrations of D18 and D20 in water. The leached amount of D18 and D20 was recalculated as a percent of the original amount impregnated into the samples before leaching.

Table 2 shows that the samples treated with both preservative solutions containing the additives of this invention were significantly more leach-resistant than their counterpart samples treated with the D18 or D20 solutions without additives. The additives increased the leaching resistance of wood treated with D18 by 51-57%, and the wood treated with D20 by 17-27%. These figures correspond well with the relatively higher water solubility of D20 (1000 ppm) compared to the lower solubility of D18 (170 ppm).

The concentration of additives used in this test was not very high and could be increased according to the concentration limits for the additives defined above. The penetrability was not retarded by the additives.

TABLE 2

Cumulative Percent Preservative Leached from Wood

| Hours of Exposure | D18 | D18+Additives | D20 | D20+Additives |
|---|---|---|---|---|
| 10 | 14 | 8 | 10 | 17 |
| 30 | 27 | 14 | 38 | 28 |
| 70 | 43 | 21 | 54 | 41 |
| 140 | 56 | 27 | 61 | 51 |

EXAMPLE 10

Effectiveness against Decay Fungi

The fungicidal activity of these compositions was determined in an accelerated experiment with the wood-rotting basidiomycetes *Lenzites trabea* (S644), *Coniophora puteana* (A302) and *Poria monticola* (A384) as test fungi. Small cross-the-grain sections of spruce wood (*Picea glauca*, a refractory species) were cut 40 microns thick on a microtome. All treatment specimens (0.5 × 0.5 inch) were cut from the same block of wood and were therefore homogeneous in nature. Wood specimens were treated to different retention levels with the active ingredients D18 or D20 with or without the additives. Two of each treatment series were placed on sterilized glass microscopic cover slips (22 mm$^2$) which were then deposited upon cultures of actively growing decay fungi in Petri dishes. Cultures were grown on a 2% malt extract, 2% agar medium. Two untreated specimens were included in each culture dish as controls. Treatment series were 0.1, 0.5 and 1.75 pcf. Incubation was for 19 days at 27° C. Each test was done in duplicate. Evaluation of the treated samples was made using a stereoscopic microscope (× 10.5 magnification). The percentage of the surface area of each specimen colonized by the test fungus was determined. The smaller the colonized surface area on each wood specimen, the more efficient the preservative composition used for specimen treatment.

TABLE 3

Average Percentage of Wood Area Colonized by Test Fungi after 19 Days Incubation at 27° C

| Test Fungus | Preservative | Retention of solids in preservatives (pcf) | | | non-treated controls |
|---|---|---|---|---|---|
| | | 0.1 | 0.5 | 1.75 | |
| *Lenzites trabea* | D18 | 25* | 0 | 0 | 100 |
| | D18+additives | 25* | 0 | 0 | 100 |
| | D20 | 50 | 0 | 0 | 100 |
| | D20+additives | 20 | 0 | 0 | 100 |
| *Coniophora puteana* | D18 | 30 | 5 | 5 | 100 |
| | D18+additives | 5 | 2.5 | 0 | 100 |
| | D20 | 40 | 10 | 10 | 100 |
| | D20+additives | 8 | 2.5 | 0 | 100 |
| *Poria monticola* | D18 | 40* | 0 | 0 | 100 |
| | D18+additives | 15* | 0 | 0 | 100 |
| | D20 | 50 | 15 | 10 | 100 |
| | D20+additives | 15 | 5 | 5 | 100 |

*Mycelia in these cases extended over the top of the treated specimens but did not colonize all of the substrate underneath.

Inclusion of the additives in the compositions studies did not reduce the effectiveness of the fungicides when compared to the compositions without additives (in most cases showed slight improvement — see Table 3). *Coniophora puteana*, which was generally more resistant to D18 and D20 than the other two fungi, grew less on the specimens treated with the fungicides containing the additives than on those specimens treated with the fungicides without the additives. This was particularly noticeable at the lowest retention level of 0.1 pcf of the chemicals.

An increase in the effectiveness of D20 due to the additives was, in addition, obtained in the test with *poria monticola* and *Lenzites trabea* (Table 3). Growth on specimens treated with D18 with or without additives at 0.1 pcf resulted, for the most part from mycelia growing over the specimens rather than on them.

EXAMPLE 11

Two series of 5 wood samples were treated under comparable conditions with two preservative formulations:

5% (w/cv) D18 in chloroform and
5% (w/v) D18 with 1.4% wax and 1% polystyrene in chloroform solution.

Initial preservative retentions were in the range 1.48–1.52 mg/cm$^3$. After solvent removal by slow air drying and a short period of oven drying both series of samples were exposed to leaching in water under the same conditions (time of exposure, temperature and volume of water for leaching). The residual amount of preservative left in the sample was determined from the difference between the original retention of the preservative and its amount present in the leaching water defined spectrophotometically. After leaching the samples were further tested for toxicity against a wood-decaying fungus in a modified standard method of testing wood preservatives by laboratory soil-block cultures. Five untreated controls and 5 samples from each preservative series were put into soil jars on wooden feeder blocks inoculated with a standard test fungus *Poria monticola*. Each of the five culture jars contained one untreated control, one spcimen treated with D18 and one specimen treated with D18+additives. Jars were located in an incubation room maintained at 80° F. and 70% R.H. and were opened one by one in five consecutive time intervals, after 25 — 32 — 39 — 46 and 65 days incubation. Wood specimens taken from the jars were oven dried and the weight loss due to decay calculated. The results are summarized in the following Table 4.

TABLE 4

Cumulative Percent Weight Loss Due to Decay

| Days of Incubation | Untreated Control | D18 | D18+Additives |
|---|---|---|---|
| 25 | 5 | 2 | 1.5 |
| 32 | 14 | 4 | 2 |
| 39 | — | 6 | 2 |
| 41 | 32 | — | — |
| 45 | — | — | 2.5 |
| 46 | 35 | 10 | — |
| 65 | 50 | 21 | 3.5 |

This experiment proves that the additives play an important role in increasing leaching-resistance of the active preservative component in treated wood. The formulation of the invention extends the toxicity of treated wood to decay fungi, thus prolonging the service life.

EXAMPLE 12

Test of Solubility of Oxathiins in Various Solvents

Table 5 is a solubility chart summarizing a list of organic solvents solubilizing oxathiins and the two additives which can be applied in the same solution.

TABLE 5

Solubility Chart

| Solvent | oxathiins | | additives | |
|---|---|---|---|---|
| | D18 | D20 | wax | polystyrene |
| Methylene chloride | + | + | + | + |
| Chloroform | + | + | + | + |
| Benzene | + | + | + | + |
| Toluene | + | + | + | + |
| Xylene | + | + | + | + |
| Propanol | + | — | + | — |
| Carbon tetrachloride | + | ⁻(+) | + | + |
| Perchloroethylene | + | ⁻(+) | + | + |
| Water | 170 ppm | 1000 ppm | — | — |

Tests with the formulations in methylene chloride and in chloroform solutions indicated the solutions were stable in the presence of iron, i.e. could be handled in iron or steel equipment.

EXAMPLE 13

Comparative tests have been completed on wood samples treated with a deep penetration preservative formulation with and without the two additives described herein. The treated samples were leached in water and then exposed to a wood-decaying fungus under standard testing conditions. The loss of sample weight was used as a measure of preservative efficiency (the lower the weight of wood sample, the lower the preservative efficacy). To obtain data on preservative performance in an accelerated laboratory test, the concentration of the preservative (DCMO) was chosen to deposit close to the known threshold level (1.1 mg/cm$^3$). Accelerated testing of a preservative at or close to its threshold level is a routine mode of testing but this level does not conform to the concentration of preservative to be used in practice. In the following tests, the components (preservative agent, wax, amorphous vinylic polymer) were in typical proportions as taught in the above application.

Sixty samples ($\frac{3}{4} \times \frac{3}{4} \times \frac{1}{4}$ inch) of homogeneous white pine were divided into three groups. One group of twenty samples (A) was used as controls not treated with the preservative. These control samples were treated only with the solvent (chloroform). The second group of samples (B) was treated with an oxathiin biocide 2,3-dihydro-5-carboxanilido-6-methyl-1,4-oxathiin (=DCMO) in 1.25% w/v solution in chloroform. The third group of samples (C) was treated with the same concentration (i.e. 1.25% w/v) ov DCM) in chloroform containing also 0.35% w/v of paraffin wax and 0.25% w/v of amorphous polystyrene (i.e. containing the additives of the invention). The samples were deeply penetrated with the solutions.

Samples were oven-dried before preservative treatment and their oven-dry weight was recorded. After the treatment with the solutions described above, the samples were again air-dried for 72 hours and oven-dried for 10 minutes at 105° C. The oven-dry weight of treated samples was recorded and retentions of preservative were calculated individually for samples B and samples C. In samples C, the content of additives was subtracted from the total retention and only the DCMO retention was compared. Average DCMO initial retentions in sample groups B and C were very close as follows:

Samples B — 1.48 mg DCMO/cm$^3$ of wood
Samples C — 1.52 mg DCMO/cm$^3$ of wood

All series of samples (A, B and C) were then leached in water. One hundred ml of water was used for each single sample (standing still 15 minutes without shaking). After 15 minutes, the samples were taken out of the leaching water, air dried for 72 hours and oven-dried for 10 minutes at 105° C.

Figure 3:
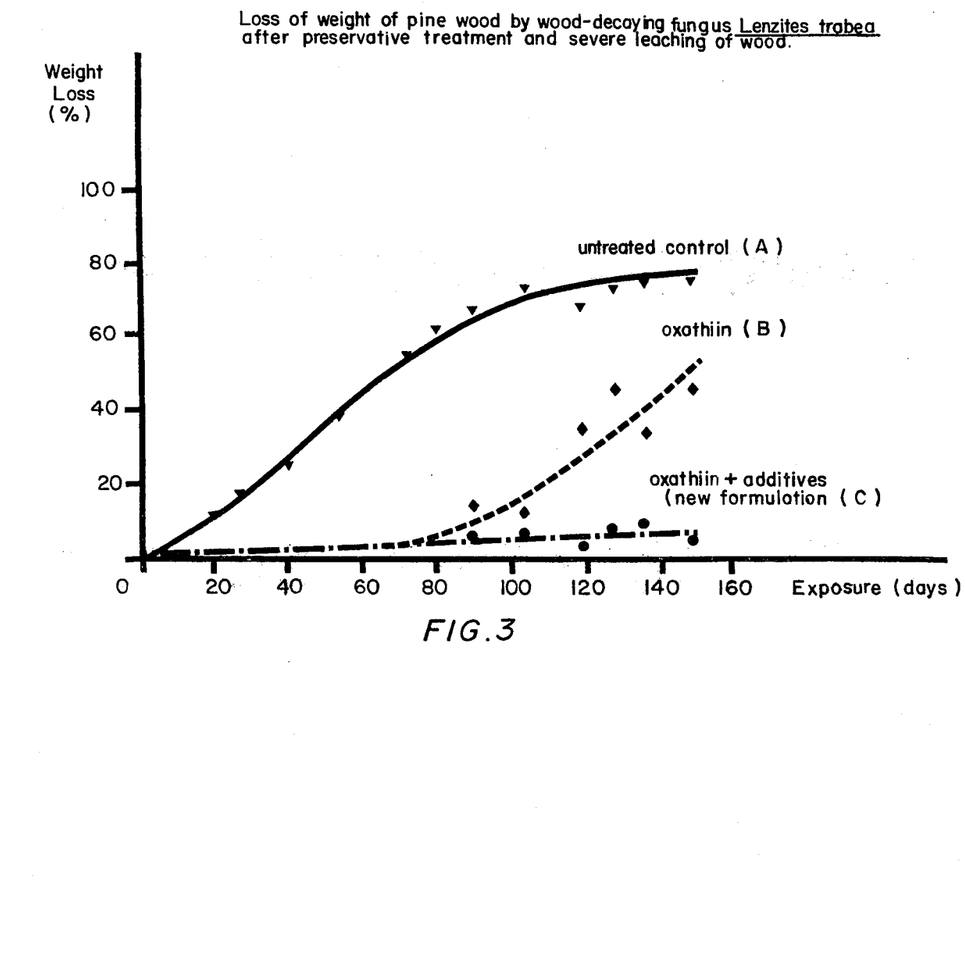
FIG. 3 is a graph showing loss of weight of wood after preservative treatment and leaching, due to wood-decaying fungus.
Figure 4:
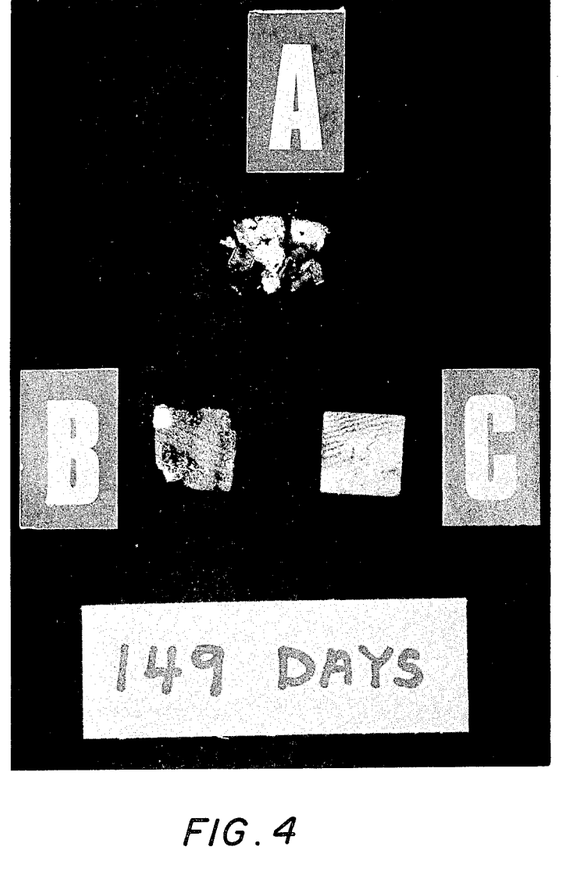
FIG. 4 is a photograph showing the cross-section of wood samples as in FIG. 3 after 149 days exposure to fungus.

The leached samples were exposed to the wood-decaying fungus *Lenzites trabea* in soil-block cultures (according to ASTM Standard D1413-76). Although this standard requires a duration of exposure of wood samples to the test fungus of three months only, tests reported here were carried out for a total of five months (149 days). During the exposure of samples in individual jars to the wood-decaying fungus, some individual samples were, at certain time intervals, taken out from the jars for the evaluation of the weight loss due to rot and wood decomposition. Other samples were left in jars to continue the test. The exposure to the fungus was finished after 149 days when residual samples in all three groups (A, B and C) were taken from jars, and the weight loss measured on oven-dried residual samples. A percent weight loss was calculated and plotted against the time of exposure (see FIG. 3 attached). Typical samples from all three groups (A, B and C) were photographed after completion (149 days) of the soil block test (see FIG. 4 attached). FIG. 4 shows a block of wood from the group of control samples A (treated with the solvent only). Block B is an example of the wood samples treated with the DCMO only, showing considerable decay. Block C is an example of the wood samples treated with the DCMO and additives (i.e. containing the additives of this invention) and was still in sound condition. This FIG. 4 illustrates the results in the FIG. 3, for the three plotted points for weight loss after 149 days of exposure.

These test data show that the presence of applicant's selected additives bestows an unexpected extension of resistance to wood decay on prolonged exposure to severe decay conditions.

Long term outdoor exposure test. Deterioration of unprotected wood due to outdoor weather and light results in a fast darkening of the wood surface, from pale yellow or light yellow-brown (natural discoloration) into intensive gray, with an incipient degradation of the mechanical macrostructure of wood (cracking or splitting) and/or incipient decay. On the other hand, well-protected wood is not subject to these changes, or these changes are minor and do not lower the value or performance of the wood commodity.

The formulation that is the subject of this invention, was tested in two further experiments, with treatments applied to wood by non-pressure processes. Two commodities were tested, white spruce siding and western red cedar shingles. The results reported here summarize observations after five years of outdoor exposure.

EXAMPLE 14

Exposure of White Spruce Siding

White spruce siding, tongue-and-groove boards 1 × 6 × 120 inch with moisture content approximately 25 to 30% were arranged into two vertical panels, each having 15 boards. One panel was facing northeast the other southwest. Each board was treated before assembling into the panel by brushing two subsequent coats of preservative formation, leaving two days between coats for sufficient solvent evaporation off the surface from the first treatment. Additionally, two boards in the middle of each panel were not treated. Five boards were not treated and not exposed, as controls. They were covered with a dark paper and kept inside.

The preservative composition, according to this invention, contained:

pentachlorophenol 5% w/v (the preservative component)
paraffin wax 3.5% w/v (water repellent component)
polystyrene 1.0% w/v (soluble amorphous polymer component)

dissolved in perchloroethylene. When the solvent was evaporated after the second coat (in 3 days, at approximately 15° C.) from the surface of the boards, the boards were assembled into the panels and placed on exposure about one foot high from the ground level.

After five years of continuous exposure, without any protection against weather (i.e. rain, sunshine, temperature changes, etc.) the boards were inspected and performance of the preservative composition evaluated. Inspections were also carried out every year during this five year period. The results, are as follows:

Untreated boards started to darken in the second and third year of exposure. After five years, their surface became dark gray, with light silver luster. In some boards, fine cracks developed. Their width was from 0.5 to 2.0 mm. Boards treated with the preservative composition retained almost their original appearance. Only a yellowish pink tint had developed, slightly changing the original tone of color during the second year of exposure. This minor change remained constant during the next few years until the time of final examination after five years. The color tone resembled the light-colored western red cedar sapwood. This change of color tone from pale yellow (a typical tone of white spruce) to the light yellowish pink is rather pleasant and from a commercial point of view has the definite advantage of a more acceptable appearance of the wood commodity. No cracks were observed on these treated boards. No signs of any decay were observed for both variants of exposed siding.

EXAMPLE 15

Exposure of Western Red Cedar Shingles

Western red cedar shingles, approximately 12-16 inch long, with variable width from approximately 7 to 12 inches were treated in a non-pressure process by soaking after preceeding vacuum treatment. Two formulations were used. One, plain preservative; and two, preservative formulation consisting of preservative plus additives according to this invention. The control samples were not treated. The treatment consisted of placing the samples into a treating retort, drawing vacuum of 22 inch Hg (that was held for 30 minutes), letting the preservative replace the vacuum and soaking in the retort. The vacuum pump was switched off after the vacuum period. The soaking, following the vacuum treatment, lasted 1 hour. This process was applied in the treatment with the plain preservative (5% w/v pentachlorophenol in perchloroethylene) as well as in the treatment with the new formulation. The composition tested was:

pentachlorophenol 5.0% w/v
paraffin wax 1.4% w/v
polystyrene 1.0% w/v dissolved in perchlorethylene. After soaking, the shingles were air dried at room temperature (approximately at 20° C.) for two weeks, well spread to allow the solvent to completely evaporte. Ten shingles of each variant (i.e. untreated controls, shingles treated with preservative only and shingles treated with preservative plus additives) were placed on an exposure rack, about 3 feet above the groundline, with southwest exposure. The shingles were inspected every year. Summary of the inspection after five years of exposure is as follows:

The untreated controls were uniformly dark gray, with occasional small cracks (in width from 1.0 mm to 3.0 mm) at the thinner edge of the shingles and some minor cracks at the thicker edge of the shingles (from 1.0 to 2.0 mm width). The pentachlorophenol treated shingles showed signs of gray discoloration unevenly distributed on the surface, but covering large portions of the surface. Some cracks were observed as well (they were in the same range of width as stated under "untreated controls"). The shingles treated with the composition according to this invention were uniformly light, showing no signs of discoloration at all. The tint of the color was almost the same as immediately after treatment. Very rarely some cracks were observed at the thinner end of several shingles, of the width approximately 0.5 mm. No signs of any decay were observed in all three variants of exposed shingles.

The preservative can be prepared in the form of a masterbatch or concentrate (without the organic solvent) or as a paste with small amounts of the organic solvent - adapted for dilution to form the final solution at the jobsite. The invention thus includes a wood preservative concentrate, soluble in lipophilic woodpenetrating organic solvents, comprising
(a) an organic wood preservative agent in from 1 to about 10 parts by weight;
(b) a hydrophobic agent selected from the group consisting of fatty acids and their esters, fatty alcohols and paraffin waxes in from about 0.5 to about 5 parts by weight, said fatty acids and alcohols having at least 10 carbon atoms in the molecule; and
(c) an amorphous vinylic-type polymer, soluble in said penetrating organic solvent, in from about 0.2 to about 1 part by weight.

I claim:

1. A penetrating wood preservative solution, causing penetration and substantial immobilization of the preservative agent within the wood, comprising:
   (a) an organic wood preservative agent in dissolved amounts of at least 1% w/v based on the solution;
   (b) a hydrophobic agent selected from the group consisting of fatty acids and their esters, fatty alcohols and paraffin waxes in amounts of from about 0.5% up to about 5% w/v based on the solution, said fatty acids and alcohols having at least 10 carbon atoms in the molecule;
   (c) an amorphous vinylic-type polymer in amounts of at least about 0.2% w/v up to about 1% w/v based on the solution, said polymer being soluble in the solution; and
   (d) a penetrating organic solvent for (a), (b), and (c).

2. The wood preservative solution of claim 1 wherein the wood preservative agent is selected from the group consisting of pentachlorophenol, an oxathiin biocide and tributyl tin oxide.

3. The wood preservative solution of claim 1 wherein the polymer is selected from the group consisting of soluble polystyrenes, soluble polymethacrylates, soluble atactic polypropylenes, and soluble polyvinylformals.

4. The wood preservative solution of claim 1 wherein the amount of polymer ranges from about 3% to about 30% of the weight of total solids in said composition.

5. The wood preservative solution of claim 3 wherein the amount of polymer ranges from about 5% to about 20% of the weight of total solids of said composition.

6. The wood preservative solution of claim 5 wherein the polymer is a soluble polystyrene.

7. The wood preservative solution of claim 1 wherein the wood preservative agent is pentachlorophenol.

8. The wood preservative solution of claim 1 wherein the wood preservative is an oxathiin compound biocide.

9. A wood preservative concentrate, soluble in lipophilic wood-penetrating organic solvents, comprising:
   (a) an organic wood preservative agent in from 1 to about 10 parts by weight;
   (b) a hydrophobic agent selected from the group consisting of fatty acids and their esters, fatty alcohols and paraffin waxes in from about 0.5 to about 5 parts by weight, said fatty acids and alcohols having at least 10 carbon atoms in the molecule, and
   (c) an amorphous vinylic-type polymer, soluble in said penetrating organic solvent, in from about 0.2 to about 1 part by weight.

10. The concentrate of claim 9 wherein the wood preservative agent is present in from about 3.5 to 5 parts by weight.

11. The concentrate of claim 10 including sufficient of said lipophilic penetrating organic solvent to form a paste.

* * * * *